United States Patent
Wulff-Döring et al.

[11] Patent Number: 5,958,825
[45] Date of Patent: Sep. 28, 1999

[54] CATALYSTS FOR THE AMINATION OF ALKYLENE OXIDES, ALCOHOLS, ALDEHYDES AND KETONES

[75] Inventors: Joachim Wulff-Döring, Frankenthal; Johann-Peter Melder, Neuhofen; Gerhard Schulz, Ludwigshafen; Guido Voit, Schriesheim; Frank Gutschoven, Gent; Wolfgang Harder, Weinheim, all of Germany

[73] Assignee: BASF Aktiengesellschaft, Ludwigshafen, Germany

[21] Appl. No.: 08/955,121

[22] Filed: Oct. 21, 1997

[30] Foreign Application Priority Data

Oct. 31, 1996 [DE] Germany ............... 196 45 047

[51] Int. Cl.$^6$ ............ B01J 23/00; B01J 23/58; B01J 23/72; B01J 23/42
[52] U.S. Cl. ............ 502/300; 502/325; 502/326; 502/328; 502/329; 502/330; 502/331; 502/333; 502/334; 502/335; 502/336; 502/337; 502/338; 502/339
[58] Field of Search ............ 502/300, 304, 502/305, 307, 308, 309, 310, 313, 314, 315, 316, 317, 318, 319, 321, 323, 324, 325, 327, 329, 330, 333–352

[56] References Cited

U.S. PATENT DOCUMENTS

| | | |
|---|---|---|
| 4,014,933 | 3/1977 | Boettger et al. ............ 260/563 R |
| 4,152,353 | 5/1979 | Habermann ............ 260/585 B |
| 4,171,287 | 10/1979 | Keith ............ 502/333 |
| 4,701,434 | 10/1987 | Koll ............ 502/230 |
| 4,727,052 | 2/1988 | Wan et al. ............ 502/341 |
| 5,003,107 | 3/1991 | Zimmerman et al. ............ 564/475 |
| 5,352,835 | 10/1994 | Dai et al. ............ 502/337 |
| 5,516,851 | 5/1996 | Flick et al. ............ 502/159 |

FOREIGN PATENT DOCUMENTS

| | | |
|---|---|---|
| 146 508 | 6/1985 | European Pat. Off. . |
| 254 335 | 1/1988 | European Pat. Off. ....... B01J 27/128 |
| 356 046 | 2/1990 | European Pat. Off. . |

*Primary Examiner*—Mark L. Bell
*Assistant Examiner*—Patricia L. Hailey
*Attorney, Agent, or Firm*—Keil & Weinkauf

[57] ABSTRACT

A catalyst comprising, based on the total weight of the catalyst, more than 6–50% by weight of cobalt, nickel or a mixture thereof, 0.001–25% by weight of ruthenium, 0–10% by weight of copper and 0–5% by weight of promoters on a porous metal oxide carrier can be prepared by (a) impregnating the carrier with the metals, promoters or compounds thereof, (b) drying and calcining the impregnated carrier and (c) reducing the calcined carrier in a stream of hydrogen, carrier not being impregnated with halogen compounds.

5 Claims, No Drawings

CATALYSTS FOR THE AMINATION OF ALKYLENE OXIDES, ALCOHOLS, ALDEHYDES AND KETONES

The present invention relates to ruthenium-, nickel- and/or cobalt-containing catalysts which can be used for aminating alkylene oxides, alcohols, aldehydes and ketones. The present invention furthermore relates to processes for the preparation of the catalysts, the use thereof in amination reactions and processes for the preparation of amination products.

EP-A2-0 146 508 discloses dehydrogenation/hydrogenation catalysts which contain ruthenium, nickel and/or cobalt. The catalysts used contain about 0.25–1.0% by weight of ruthenium and 7.5 or 10% by weight of nickel or 10% by weight of cobalt or 4% by weight of nickel and 4% by weight of cobalt, based on the total weight of the catalyst, on an alumina carrier. The catalysts may also contain copper and chromium in addition to nickel, and also iron in addition to nickel and cobalt. The ruthenium is applied to the catalyst in the form of a solution of a ruthenium halide. The catalyst is used, for example, for aminating monoethanolamine with ammonia, the reaction being carried out in an autoclave.

EP-A1-0 254 335 discloses a process for the preparation of a hydrogenation and/or dehydrogenation catalyst, about 10% by weight of nickel or cobalt and about 0.5% by weight of ruthenium, based on the total weight of the catalyst, being applied to an alumina carrier. The catalyst is prepared by impregnating the carrier with a nickel nitrate or cobalt nitrate solution, then impregnating with aqueous hydrochloric acid and subsequently impregnating with a solution of ruthenium nitrosyl nitrate. A ruthenium halide is not used for impregnating the carrier. The catalyst is used for reacting monoethanolamine with ammonia in an autoclave.

The known catalysts have chloride contents introduced by impregnation. Both during the catalyst preparation and during reactions using the catalyst, chlorides present on the catalyst carrier may lead to corrosion problems if, for example, hydrochloric acid is liberated from the catalyst. Moreover, the stability is insufficient, particularly in the case of the catalysts described in EP-A1-0 254 335. The impregnation of the carrier with an aqueous hydrochloric acid, as described in EP-A1-0 254 335, leads to poorer mechanical properties of the catalyst since the oxidic carriers are attacked by the acid. As a result, the mechanical stability of the catalyst is reduced so that the life of the catalyst in operation decreases considerably owing to catalyst disintegration. The selectivities obtained in the reaction of monoethanolamine with ammonia, with respect to ethylenediamine, are insufficient for a continuous procedure.

It is an object of the present invention to provide amination catalysts which avoid the disadvantages of the known catalysts and in particular do not cause corrosion and at the same time have good stability and high selectivity with respect to ethylenediamine in the amination of monoethanolamine with ammonia.

We have found that this object is achieved by providing a catalyst comprising, based on the total weight of the catalyst, more than 6–50% by weight of cobalt, nickel or a mixture thereof,
0.001–25% by weight of ruthenium,
0–10% by weight of copper and
0–5% by weight of promoters selected from the group consisting of iron, rhodium, palladium, platinum, iridium, osmium, silver, gold, chromium, molybdenum, tungsten, rhenium, zinc, cadmium, lead, manganese, tin, lithium, sodium, potassium, rubidium, caesium, phosphorus, arsenic, antimony, bismuth, tellurium, thallium or mixtures thereof on a porous metal oxide carrier, which can be prepared by (a) impregnating the carrier with the metals, promoters or compounds thereof,
(b) drying and calcining the impregnated carrier and
(c) reducing the calcined carrier in a stream of hydrogen, the carrier not being impregnated with halogen compounds.

The catalyst carrier preferably used is a porous metal oxide which is selected from the group consisting of alumina, aluminosilicates, titanium dioxide, zirconium dioxide, magnesium oxide and mixtures thereof.

Carriers which contain alumina are preferably used, particularly preferably those consisting of alumina.

More than 6–50, preferably more than 6–40, in particular more than 6–20, % by weight of cobalt, nickel or a mixture thereof are applied to the catalyst carrier. The stated weights are based on the total weight of the catalyst, unless stated otherwise. Preferably more than 3–25, particularly preferably more than 3–20, in particular more than 3–10, especially 5–10, % by weight of cobalt are applied to the carrier. Furthermore, preferably more than 3–25, particularly preferably more than 3–20, in particular more than 3–10, especially 5–10, % by weight of nickel are applied.

The catalyst furthermore contains 0.001–25, often 0.01–25, preferably 0.1–10, particularly preferably 0.5–5, in particular 0.5–2, % by weight of ruthenium on the carrier.

Copper may also be applied to the carrier. The copper content is 0–10, preferably 0.1–10, particularly preferably 0.5–5, % by weight.

0–5% by weight of promoters may also be present on the carrier. They are selected from the group consisting of iron, rhodium, palladium, platinum, iridium, osmium, silver, gold, chromium, molybdenum, tungsten, rhenium, zinc, cadmium, lead, manganese, tin, lithium, sodium, potassium, rubidium, caesium, phosphorus, arsenic, antimony, bismuth, tellurium, thallium and mixtures thereof.

Particularly preferably, the catalyst contains 5–10% by weight of cobalt, 5–10% by weight of nickel, 0.5–5% by weight of ruthenium and 0.5–5% by weight of copper. In particular, the content of nickel is 7– 9% by weight, that of cobalt 7–9% by weight, that of copper 1.3–1.9% by weight and that of ruthenium 0.5–1.5% by weight.

The selectivity of the catalyst can be controlled by additional doping of the catalyst carrier with the abovementioned promoters. The promoter content is preferably 0.001–5, in particular 0.01–3, % by weight.

The catalysts are prepared by (a) impregnating the carrier with metals, promoters or compounds thereof,
(b) drying and calcining the impregnated carrier and
(c) reducing the calcined carrier in a stream of hydrogen.

Below, the metals and the promoters are discussed and are together referred to as metals.

The carrier can be impregnated with the metals or compounds of the metals in step (a) by any desired suitable method. For example, the carrier may be impregnated with a solution of the metal compounds. Impregnation of the carrier may also be effected by spraying on the solutions or kneading the carrier together with the solutions or by precipitating the metals or metal compounds onto the carrier.

The metals with which the carrier is impregnated are preferably used in the form of a solution of the halide-free salts of the metals. For example, the nitrates, formates, oxalates or ammoniates may be used, preferably the oxalates and nitrates, particularly preferably the nitrates.

The carrier is not impregnated with halogen compounds. In particular, the carrier is not impregnated with metal halides or solutions of the metal halides or with another halide-containing solution, such as aqueous hydrochloric acid solution.

This avoids the problems described at the outset and gives an advantageous catalyst.

The impregnation of the catalyst with metals or metal salt solutions can be carried out in any desired order. For example, the catalyst carrier can be impregnated with a solution which contains all metal salts. The carrier may also be impregnated in succession with a plurality of solutions which contain the salts of one or more of the metals used. All or individual impregnation layers may be applied several times, it being possible to change the order of the impregnations. In the case of multiple impregnations, in particular when the solutions are sprayed on several times or the carrier impregnated several times with the solutions, the concentration of the metal salts in the solutions may be kept low.

The concentration in the solutions or solution can also be established so that the desired amount of metal is present on the carrier as a result of a single application or impregnation. After the impregnation of the carrier with the metals or compounds of the metals, the impregnated carrier is preferably dried at 80–150° C., particularly preferably 80–120° C. The impregnated carrier is then calcined at 150–500° C., preferably 300–500° C. The impregnated and calcined carrier is then reduced in a stream of hydrogen at 150–500° C., preferably 200–400° C. For this purpose, the carrier is preferably first cooled after the calcination. The stream of hydrogen may be used as a pure hydrogen stream or as a dilute hydrogen stream, for example in an inert gas, such as nitrogen.

The reduction, which may also be referred to as activation, can be carried out directly in the reactor which is used for the subsequent synthesis. If the reduction of the catalysts is carried out in a separate reactor, the catalysts are superficially passivated before being removed from the reactor, preferably at 10–60° C., in particular 20–40° C., with a gas mixture which contains free oxygen. After installation in the reactor intended for the synthesis, the catalysts passivated in this manner may be activated in a stream of hydrogen, preferably a nitrogen/hydrogen stream, at 150–200° C., preferably 170–190° C. They can also be used without further activation.

The novel catalysts can be used in any suitable form, for example as moldings, such as extrudates or pellets, or in powder form. The shaped carriers may be impregnated with the metals or metal compounds, or impregnated carriers may be brought to the desired shape. When carrier and metals or metal compounds are kneaded together or precipitated together, the resulting materials are as a rule subsequently molded. Particularly in the continuous procedure, the catalysts are used in the form of moldings.

The novel catalysts can be used in a large number of reactions. According to the invention, they are preferably used in hydrogenation reactions, dehydrogenation reactions or hydrogenation/dehydrogenation reactions. In particular, the catalysts are used for aminating alkylene oxides, alcohols, aldehydes or ketones with ammonia or primary or secondary amines. Particularly preferably, the catalysts are used for aminating alcohols, especially in the reaction of monoethanolamine with ammonia to give ethylenediamine. The novel catalysts are mechanically stable over a long time and show no decrease in activity. In combination with the same activity as the known catalysts having a high content of nickel and cobalt, they exhibit higher selectivity with regard to the formation of primary amination products in the amination with ammonia. They also have a substantially improved life and do not release any corrosive compounds.

The present invention also relates to a process for the preparation of amination products by reacting alkylene oxides, alcohols, aldehydes or ketones with ammonia or primary or secondary amines in the presence of free hydrogen and in the presence of a catalyst as described above.

The amination is carried out by reacting ammonia or a primary or secondary amino group with a hydroxyl group, an aldehyde or keto group or an alkylene oxide group, aldehyde, keto or alkylene oxide groups undergoing reductive amination and hydroxyl groups being replaced by amino groups. The amino groups and groups to be aminated may be present in different molecules or in the same molecule. If the groups to be reacted with one another are present in the same molecule, cyclic compounds may result. The compounds in which amino groups and groups to be aminated are present may furthermore act either as an amine component or as a compound to be aminated.

For example, inter alia, ethylenediamine (EDA), aminoethylethanolamine (AEEA), diethylenetriamine (DETA) and piperazine may be obtained in the amination of monoethanolamine (MEA) with ammonia.

It is also possible to use compounds which have two or more of the hydroxyl, aldehyde, keto or alkylene oxide groups. Mixed groups may also be present. In particular, diols or polyols may be used, especially ethylene glycols. Other suitable compounds are those which have a plurality of primary or secondary amino groups, such as alkylenediamines, in particular ethylenediamine. For example, ethylene glycols or ethanolamines can be aminated with, or in the presence of, ammonia, ethanolamines, ethylenediamines or diethylenetriamines.

In one embodiment of the invention, the novel process is used for the preparation of amines of the general formula (I)

$$R^1R^2N\text{---}CHR^3R^4 \qquad (I)$$

where $R^1$, $R^2$, $R^3$ and $R^4$ independently are each hydrogen, $C_1$–$C_{200}$-alkyl, $C_3$–$C_{12}$-cycloalkyl, amino-, $C_1$–$C_{20}$-alkylamino-, di-$C_1$–$C_{20}$-alkylamino- and/or hydroxyl-substituted $C_1$–$C_{20}$-alkyl, $C_2$–$C_{30}$-alkoxyalkyl, $R^5(OCHR^6CH_2)_n$, aryl, $C_7$–$C_{20}$-aralkyl or $C_7$–$C_{20}$-alkylaryl, or $R^1$ and $R^2$ together form $(CH_2)_l$—X—$(CH_2)_m$, where $R^5$ is hydrogen or $C_1$–$C_4$-alkyl, $R^6$ is hydrogen or methyl, X is oxygen or $NR^6$, n is an integer from 2 to 30, l is an integer from 2 to 4 and m is an integer from 1 to 4, from primary or secondary alcohols, ketones, aldehydes of the general formula (II)

$$R^3R^4CHOH \text{ or } R^3R^4CO \qquad (II)$$

where $R^3$ and $R^4$ have the abovementioned meanings, and primary or secondary amines of the general formula (III)

$$R^1R^2NH \qquad (III)$$

where $R^1$ and $R^2$ have the abovementioned meanings.

$R^1$, $R^2$, $R^3$ and $R^4$, in particular $R^1$ and $R^2$, may be $C_1$–$C_{200}$-alkyl, preferably $C_1$–$C_8$-alkyl, such as methyl, ethyl, n-propyl, isopropyl, n-butyl, isobutyl, sec-butyl, tert-butyl, n-pentyl, isopentyl, sec-pentyl, neopentyl, 1,2-dimethylpropyl, n-hexyl, isohexyl, sec-hexyl, n-heptyl, isoheptyl, n-octyl, isooctyl, 2-ethylhexyl, n-decyl, 2-n-propyl-n-heptyl, n-tridecyl, 2-n-butyl-n-nonyl or 3-n-butyl-n-nonyl, particularly preferably isopropyl, 2-ethylhexyl, n-decyl, 2-n-propyl-n-heptyl, n-tridecyl, 2-n-butyl-n-nonyl or 3-n-butyl-n-nonyl, or $C_{40}$–$C_{200}$-alkyl, such as polybutyl, polyisobutyl, polypropyl, polyisopropyl or polyethyl, particularly preferably polybutyl or polyisobutyl.

$R^1$ and $R^2$ together may be —$(CH_2)_l$—X—$(CH_2)_m$, where X is oxygen or N-$R^6$ having the meanings stated below and l is an integer from 2 to 4, such as 2, 3 or 4, preferably 2 or 3, particularly preferably 2, and m is an integer from 1 to 4, such as 1, 2, 3 or 4, preferably 2, 3 or 4, particularly preferably 2 or 3.

$R^1$, $R^2$, $R^3$ and $R^4$ may each be $C_3$–$C_{12}$-cycloalkyl, preferably $C_3$–$C_8$-cycloalkyl, such as cyclopropyl, cyclobutyl, cyclopentyl, cyclohexyl, cycloheptyl or cyclooctyl, particularly preferably cyclopentyl cyclohexyl or cyclooctyl.

They may be aryl, such as phenyl, 1-naphthyl, 2-naphthyl, 1-anthryl, 2-anthryl or 9-anthryl, preferably phenyl, 1-naphthyl or 2-naphthyl, particularly preferably phenyl.

They may be $C_7$–$C_{20}$-alkylaryl, preferably $C_7$–$C_{12}$-alkylphenyl, such as 2-methylphenyl, 3-methylphenyl, 4-methylphenyl, 2,4-dimethylphenyl, 2,5-dimethylphenyl, 2,6-dimethylphenyl, 3,4-dimethylphenyl, 3,5-dimethylphenyl, 2,3, 4-trimethylphenyl, 2,3,5-trimethylphenyl, 2,3,6-trimethylphenyl, 2,4,6-trimethylphenyl, 2-ethylphenyl, 3-ethylphenyl, 4-ethylphenyl, 2-n-propylphenyl, 3-n-propylphenyl or 4-n-propylphenyl.

They may be $C_7$–$C_{20}$-aralkyl, preferably $C_7$–$C_{12}$-phenylalkyl, such as benzyl, 1-phenylethyl, 2-phenylethyl, 1-phenylpropyl, 2-phenylpropyl, 3-phenylpropyl, 1-phenylbutyl, 2-phenylbutyl, 3-phenylbutyl or 4-phenylbutyl, particularly preferably benzyl, 1-phenylethyl or 2-phenylethyl.

$R^1$ may be in particular $C_1$–$C_{20}$-alkyl, preferably $C_1$–$C_8$-alkyl, such as methyl, ethyl, n-propyl, isopropyl, n-butyl, isobutyl, sec-butyl, tert-butyl, n-pentyl, isopentyl, sec-pentyl, neopentyl, 1,2-dimethylpropyl, n-hexyl, isohexyl, sec-hexyl, n-heptyl, isoheptyl, n-octyl, isooctyl, particularly preferably $C_1$–$C_4$-alkyl, such as methyl, ethyl, n-propyl, isopropyl, n-butyl, isobutyl, sec-butyl or tert-butyl.

$R^3$ and $R^4$ may be in particular $C_1$–$C_{20}$-hydroxyalkyl, preferably $C_1$–$C_8$-hydroxyalkyl, particularly preferably $C_1$–$C_4$-hydroxyalkyl, such as hydroxymethyl, 1-hydroxyethyl, 2-hydroxyethyl, 1-hydroxy-n-propyl, 2-hydroxyl-n-propyl, 3-hydroxy-n-propyl or 1-hydroxymethylethyl, or amino- and/or alkylamino- and/or dialkylamino- and/or hydroxyl-substituted $C_1$–$C_{20}$-alkyl, preferably $C_1$–$C_8$-alkyl, particularly preferably $C_1$–$C_4$-alkyl, such as N-(hydroxyethyl)aminoethyl or N-(aminoethyl)aminoethyl.

They may be $C_2$–$C_{30}$-alkoxyalkyl, preferably $C_2$–$C_{20}$-alkoxyalkyl, particularly preferably $C_2$–$C_8$-alkoxyalkyl, such as methoxymethyl, ethoxymethyl, n-propoxymethyl, isopropoxymethyl, n-butoxymethyl, isobutoxymethyl, sec-butoxymethyl, tert-butoxymethyl, 1-methoxyethyl or 2-methoxymethyl, particularly preferably $C_2$–$C_4$-alkoxyalkyl, such as methoxymethyl, ethoxymethyl, n-propoxymethyl, isopropoxymethyl, n-butoxymethyl, isobutoxymethyl, sec-butoxymethyl, tert-butoxymethyl, 1-methoxyethyl or 2-methoxyethyl.

They may be $R^5$—$(COHR^6CH_2)_n$, where $R^5$ is $C_1$–$C_4$-alkyl, such as methyl, ethyl, n-propyl, isopropyl, n-butyl, isobutyl, sec-butyl or tert-butyl, preferably methyl or ethyl, particularly preferably methyl. $R^6$ is hydrogen or methyl.

n is an integer from 2 to 10, preferably from 2 to 8, such as 2, 3, 4, 5, 6, 7 or 8, particularly preferably 2, 3, 4, 5 or 6.

All radicals $R^1$ to $R^6$ may furthermore be hydrogen.

The novel process can be carried out batchwise or, preferably, continuously. The continuous procedure is preferably carried out in a tubular reactor by the trickle-bed or liquid phase method. Particularly in the amination of alcohols, temperatures of 120–250° C., preferably 150–190° C., and pressures of 150–300, preferably 180–220, bar are employed. In general, temperatures of 80–250° C. and pressures of 100–400 bar can be employed.

In the reaction with ammonia, ammonia may be used as a reagent or as a solvent. 1–20, preferably 6–12, mol of ammonia may be used per mol of alkylene oxide, alcohol, aldehyde or ketone. The catalyst space velocity is preferably from 0.05 to 2.0, particularly preferably from 0.1 to 1.0, kg of alkylene oxide, alcohol, aldehyde or ketone per liter of catalyst per hour. The reaction may also be carried out in the presence of water, it being possible to add up to 15% by weight, based on the total reaction mixture, of water.

The use of the novel catalysts in the process according to the invention permits, in particular in the reaction of monoethanolamine with ammonia, a high yield of ethylenediamine owing to the high selectivity of the novel catalysts.

The products obtained by the novel process are suitable, inter alia, as intermediates for the preparation of fuel additives, for example described in U.S. Pat. No. 3,275,554, DE-A-21 25 039 or DE-A-36 11 230. The compounds obtained according to the invention can also be used in the preparation of surfactants, drugs and crop protection agents as well as vulcanization accelerators. The Examples which follow illustrate the invention.

EXAMPLE 1

135 g of $Al_2O_3$ extrudates having a diameter of 4 mm (D10-10, produced by BASF AG, Ludwigshafen) were left to stand with 88 ml of an aqueous impregnating solution which contained 8.88 g of NiO, 8.88 g of CoO and 3.55 g of CuO, with repeated thorough stirring at room temperature for two hours. The catalyst precursor was dried for 16 hours at 120° C. and calcined for four hours at 400° C. This process was repeated. 140 g of these extrudates were then introduced into an impregnating drum and 73.5 ml of an aqueous ruthenium nitrate solution which contained 1.57 g of ruthenium were sprayed on in the course of 10 minutes. Nickel, cobalt and copper were used in the form of the nitrates.

The catalyst precursor was then dried for 16 hours at 120° C. and calcined for four hours at 400° C. After cooling, the extrudates were installed in a reduction apparatus and flushed for two hours with 20 l of $N_2$ per hour. Heating was then carried out to 300° C. at a rate of 2° C./min and with a hydrogen flow rate of 20 l of $H_2$ per hour, and this temperature was maintained for 20 hours. After cooling in a stream of nitrogen, the catalyst was passivated with an air/nitrogen mixture, a maximum temperature increase of 20° C. being permitted. The catalyst thus prepared contained 1% by weight of ruthenium, 7.9% by weight of nickel, 7.9% by weight of cobalt and 3.2% by weight of copper on alumina. The results in the amination of monoethanolamine are listed in Table 1. The catalyst was still completely intact after an operating time of 303 hours.

Comparative Example V1

The catalyst was prepared by the process stated in EP-A1-0 254 335, Example 1. The catalyst thus obtained contained 10% by weight of nickel and 0.5% by weight of ruthenium on alumina (D10-10 from BASF AG, Ludwigshafen). The results in the amination of monoethanolamine are listed in Table 1. The catalyst had completely disintegrated after an operating time of 48 hours.

Comparative Example V2

The catalyst was prepared by the process stated in EP-A1-0 254 335, Example 13. The catalyst thus obtained contained 10% by weight of cobalt and 0.5% by weight of ruthenium on alumina (D10-10 from BASF AG, Ludwigshafen). The results in the amination of monoethanolamine are listed in Table 1. The catalyst had completely disintegrated after an operating time of 48 hours.

Amination

The amination of monoethanolamine in the presence of the catalysts of Example 1 and Comparative Examples V1 and V2 was carried out as follows: a tubular reactor having a capacity of 100 ml, a length of 55 cm and an internal diameter of 1.5 cm was filled with 50 g of passivated catalyst and the latter was activated at 180° C. first with a mixture of 20% by volume of hydrogen/80% by volume of nitrogen and then with 100% by volume of hydrogen. After the reaction temperature had been brought to 175–195° C., depending on the activity of the catalyst, the reactor was charged with 10–30 g/h of monoethanolamine, 20–70 g/h of ammonia and 3–101 (S.T.P)/h of hydrogen. The conversion and the selectivity with respect to the components ethylenediamine (EDA), aminoethylethanolamine (AEEA), diethylenetriamine (DETA) and piperazine were determined by gas chromatographic analysis of the discharge. The catalyst space velocity is stated with respect to monoethanolamine (MEA). The results are summarized in Table 1 below.

EXAMPLE 2

The catalyst described in Example 1 was used.

Amination

The amination of monoethanolamine in the presence of the catalyst was carried out as follows: a tubular reactor having a capacity of 1 l was filled with 500 ml of passivated catalyst between two layers each comprising 250 ml of V2A stainless steel rings and was started up without further pretreatment. After the reaction temperature had been established at 155–200° C., depending on the activity of the catalyst, the reactor was charged with 130–200 g/h of MEA with an MEA:NH$_3$ ratio of 1:8 and with 10–50 l (S.T.P.)/h of hydrogen. The analysis of the reactor discharge was carried out as described above. The catalyst removed after 59 days was completely intact. The results are summarized in Table 1 below.

TABLE 1

| Catalyst from | Carrier | Pressure [bar] | Temperature [°C.] | MEA space velocity [kg/l·h] | NH$_3$/MEA [mol/mol] | Conversion [%] | EDA [%] | AEEA [%] | Piperazine [%] | DETA [%] |
|---|---|---|---|---|---|---|---|---|---|---|
| Comp. Expl. V1 | Al$_2$O$_3$ | 200 | 175 | 0.45 | 8 | 33.3 | 55.60 | 20.7 | 4.90 | 12.6 |
| Comp. Expl. V2 | Al$_2$O$_3$ | 200 | 170 | 0.45 | 8 | 32.2 | 62.5 | 17.9 | 2.6 | 5.7 |
|  |  | 200 | 185 | 0.45 | 8 | 46.4 | 61.8 | 15.0 | 5.0 | 7.4 |
| Expl. 1 | Al$_2$O$_3$ | 200 | 170 | 0.45 | 8 | 32.2 | 62.5 | 17.9 | 2.6 | 5.7 |
|  |  |  | 185 | 0.45 | 8 | 46.4 | 61.8 | 15.0 | 5.0 | 7.4 |
| Expl. 2 | Al$_2$O$_3$ | 180 | 165 | 0.45 | 8 | 44.4 | 66.5 | 10.6 | 6.3 | 12.1 |

MEA = Monoethanolamine
EDA = Ethylenediamine
AEEA = Aminoethylethanolamine
DETA = Diethylenetriamine The results in Table 1 show that the selectivity in relation to ethylenediamine is substantially higher when the novel catalysts are used than when the known catalysts are used. Moreover, the stability of the novel catalysts is substantially higher than the stability of the comparative catalysts.

We claim:

1. A catalyst consisting essentially of, based on the total weight of the catalyst, more than 6–50% by weight of cobalt, nickel or a mixture thereof, 0.001–25% by weight of ruthenium, 0–10% by weight of copper and 0–5% by weight of promoters selected from the group consisting of iron, rhodium, palladium, platinum, iridium, osmium, silver, gold, chromium, molybdenum, tungsten, rhenium, zinc, cadmium, lead, manganese, tin, lithium, sodium, potassium, rubidium, caesium, phosphorus, arsenic, antimony, bismuth, tellurium, thallium or mixtures thereof on a porous metal oxide carrier, which is prepared by (a) impregnating the carrier with the metals, promoters or compounds thereof with a solution of halide-free salts of said metals, promoters, or compounds, (b) drying and calcining the impregnated carrier and (c) reducing the calcined carrier in a stream of hydrogen.

2. A catalyst as claimed in claim 1, comprising more than 3–25% by weight of cobalt and more than 3–25% by weight of nickel.

3. A catalyst as claimed in claim 1, wherein the porous metal oxide carrier is selected from alumina, silica, aluminosilicates, titanium dioxide, zirconium dioxide, magnesium oxide and mixtures thereof.

4. A catalyst as claimed in claim 1, which is essentially halogen-free.

5. A process for the preparation of a catalyst as claimed in claim 1 by (a) impregnating the carrier with the metals, promoters or compounds thereof, (b) drying and calcining the impregnated carrier and (c) reducing the calcined carrier in a stream of hydrogen.

* * * * *